United States Patent [19]

Nagai et al.

[11] Patent Number: 5,747,652
[45] Date of Patent: May 5, 1998

[54] ANTIBODY TO SMOOTH MUSCLE MYOSIN HEAVY CHAINS

[75] Inventors: Ryozo Nagai; Makoto Kuroo, both of Tokyo; Hirohisa Kato, Choshi, all of Japan

[73] Assignee: Yamasa Shoyu Kabushiki Kaisha, Chiba-ken, Japan

[21] Appl. No.: 360,127

[22] Filed: Dec. 20, 1994

Related U.S. Application Data

[63] Continuation of Ser. No. 163,407, Dec. 8, 1993, abandoned, which is a continuation of Ser. No. 768,075, filed as PCT/JP90/00398 published as WO90/11520, abandoned.

[30] Foreign Application Priority Data

Mar. 28, 1989 [JP] Japan ................................ 1-075884

[51] Int. Cl.$^6$ .................................................. C07K 16/18
[52] U.S. Cl. ..................... 530/387.9; 530/388.2; 530/389.1; 436/547; 436/548
[58] Field of Search ........................... 530/387.9, 388.2, 530/389.1; 436/547, 548

[56] References Cited

PUBLICATIONS

Roitt (1991) "Essential Immunology", Blackwell Scientific Publications, Oxford, pp. 65–68 & 74.
VanRegenmortel et al. (1990) In "Laboratory Techniques in Biochemistry and Molecular Biology", (R. H. Burdon et al. eds), Elsevier, Amsterdam, pp. 11–13.
Nicol et al (1993) J. Nucl. Med. 34(12):2144–2151.
Nagai et al (1989) J. Biol. Chem. 264(17):9734–9737.
Masaki et al (1986), In "Molecular Biology of Muscle Development" (C. Emerson et al. eds.), Alan R. Liss, Inc., N.Y., pp. 323–336.
Eddinger et al. (1988) Biochemistry 27:3807–3811.
Yanagisawa et al. (1987) J. Mol. Biol. 198:143–157.
J. of Biol. Chem., "DNA Cloning of a Myosin Heavy Chain Isoform in Embryonic Smooth Muscle and Its Expression During Vascular Development and in Arteriosclerosis", Kuro–o et al., vol. 266, No. 6, Feb. 25, 1991, pp. 3768–3733.
J. Biol. Chem., "Identification of Two Types of Smooth Muscle Myosin Heavy Chain Isoforms by cDNA Cloning and Immunoblot Analysis", Nagai et al., vol. 264, No. 17, Jun. 15, 1989, pp. 9734–9737.
Ardizzi et al., The Journal of Cell Biology, vol. 105, No. 6 (1987) pp. 2763–2770.
Mohammad et al., The Biochemical Journal, vol. 260, No. 2 (1989) pp. 421–426.
Sartore et al., Eur. J. Biochem., vol. 179, No. 1 (1989) pp. 79–85.
Borrione et al., Eur. J. Biochem., vol. 183, No. 2 (1989) pp. 413–417.
Kuro et al., The Journal of Biological Chemistry, Vo. 264 No. 31 (1989) pp. 18272–18275.

*Primary Examiner*—Toni R. Scheiner
*Attorney, Agent, or Firm*—Wenderoth, Lind & Ponack

[57] ABSTRACT

Using as an immunogen an oligopeptide containing a different portion of the amino acid sequence of isoform SM-1, SM-2 or SM-3 in smooth muscle myosin heavy chains, for example, the C-terminus amino acid sequence, antibodies capable of distinctly recognizing each isoform from other isoforms of the smooth muscle myosin heavy chains can be obtained. The antibodies are useful as reagents for tissue staining and also useful as diagnostic reagents of vascular disturbance or arteriosclerosis.

9 Claims, 9 Drawing Sheets

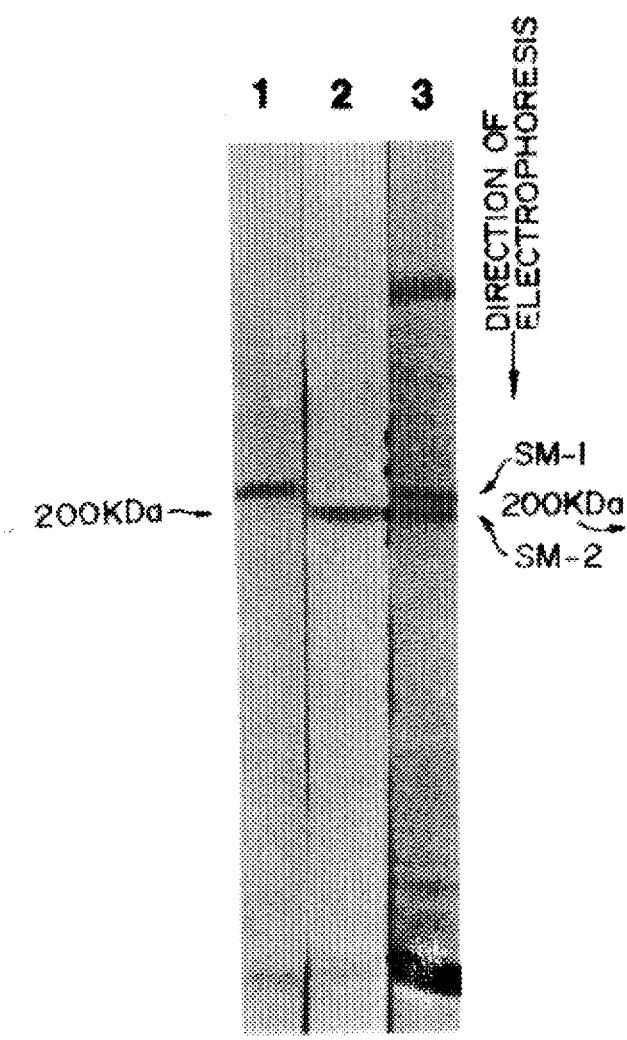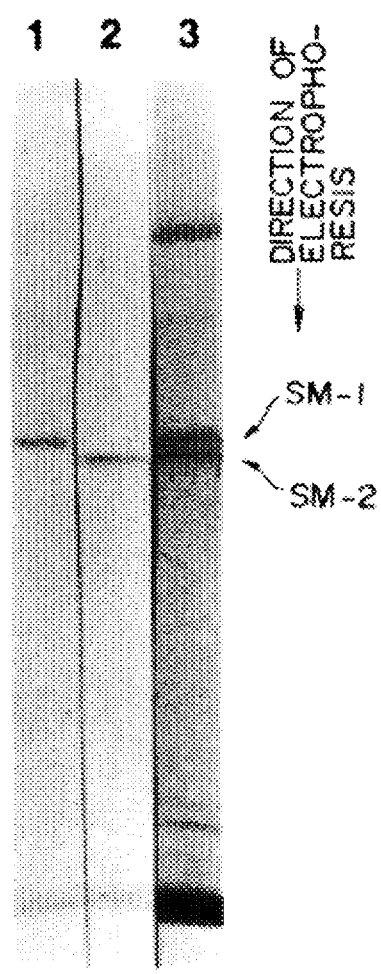

RABBIT BOTALLO'S DUCT (DAY 1 AFTER BIRTH)

AROTA OF RABBIT

AROTA OF RABBIT
| FETAL PERIOD | NEONATAL PERIOD (DAY 10 AFTER BIRTH) | GROWTH PERIOD (DAY 30 AFTER BIRTH) |
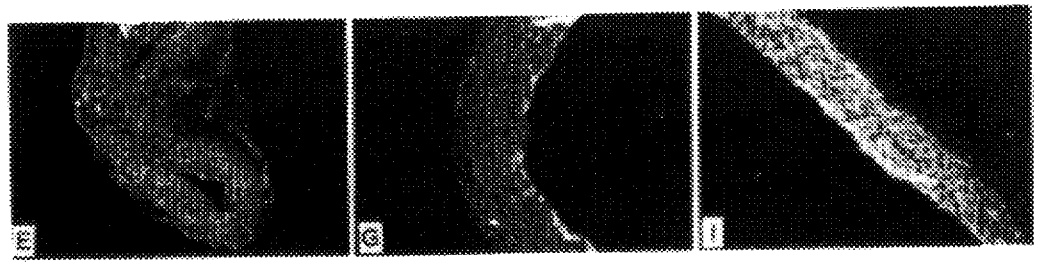
FIG. 5A          FIG. 5C          FIG. 5E
FIG. 5B          FIG. 5D          FIG. 5F
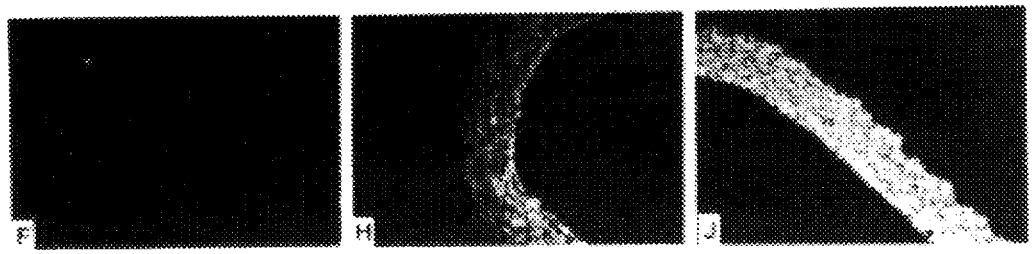

UTERUS OF RABBIT

NORMAL BLOOD VESSEL OF HUMAN ADULT

FIG. 8A
AROTA OF RABBIT
A FETAL PERIOD
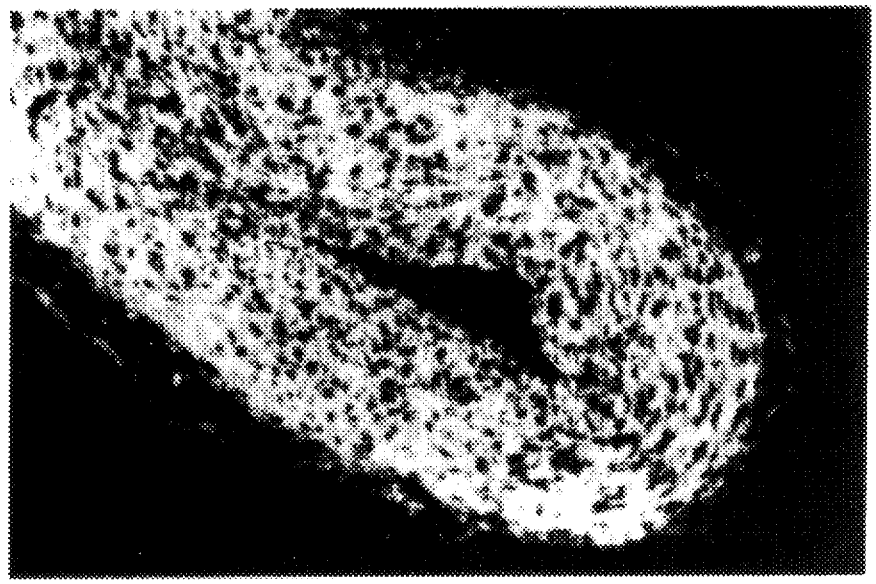
B GROWTH PERIOD
FIG. 8B

HUMAN UMBILICAL CORD ARTERY

FIG. 10

AMINO ACID SEQUENCE OF ISOFORMS IN SMOOTH MUSCLE MYOSIN HEAVY CHAINS EXCEPT FOR THE N-TERMINUS

```
SM-3 ──→
SM-1 ══➤
SM-2 ──→

1    R  E  A  R  E  K  E  T  K  A  L  S  L  S  R  A  L  E  E  A    20
       A                                   A
       A                                   A

21    L  E  A  K  E  E  F  E  R  Q  N  K  Q  L  R  A  D  M  E  D    40
                         L        T        M     K     E
                         L        T        M     K     E

41    L  M  S  S  K  D  D  V  G  K  N  V  H  E  L  E  K  S  K  R    60
          V
          V

61    A  L  E  Q  Q  V  E  E  M  R  T  Q  L  E  E  L  E  D  E  L    80
             T     M     K
             T     M     K

81    Q  A  T  E  D  A  K  L  R  L  E  V  N  T  Q  A  M  K  A  Q   100
                                           M        L     V
                                           M        L     V
                                                    R

101    F  E  R  D  L  Q  A  R  D  E  Q  S  E  E  K  K  R  L  L  T   120
                                     N              R     Q  Q
                                     N              R     Q  Q

121    K  Q  V  R  E  L  E  A  E  L  E  D  E  R  K  Q  R  A  L  A   140
       R     L  H     Y     T
       R     L  H     Y     T

141    V  A  L  K  K  M  E  I  D  L  K  D  L  E  A  Q  I  E  A      160
       A     S        L     G           L     L     A  A  D  S
       A     A        L     G           L     A  A  D  S
                                                    A  M  S

161    A  N  K  A  R  E  R  K  Q  L  R  R  L  Q  A  Q  M  K         180
          I     G  A     R  V        L  K              D
          Y     G              I        K              M
          F     G              I

181    D  Y  Q  R  E  L  E  A  R  G  S  R  D  E  I  F  A  Q  T  S   200
          F                 D     A                       T  A
          F                 D     A                       T  E

201    K  E  S  E  K  K  L  K  S  L  E  A  E  I  L  Q  L  Q  E      220
          N                 A        D  L  M     R
          N                 A        D  L  M     R
          S

221    L  A  S  E  R  A  R  R  H  A  E  D  L  M  D  E  L  A  D      240
          A  A              K  Q     D  L  R  E        E
             N              K  Q     D  L  K  E        E
             S                                K
             A
             A

241    E  I  N  S  A  S  G  K  A  L  D  E  K  R  R  L  E            260
          L     S     L        R           K              E
          L     R     L        R                          E
             G
             R
             R

261    A  I  Q  L  E  E  L  E  E  Q  S  N  M  E  L  L               280
             R                       G           A  M
                                     G           A  M
                                                 A  A
                                                    T

281    N  D  R  R  K  T  T  L  Q  V  D  T  L  A  E  L  A            300
       S           A        Q     A  E  Q     N
       S           A        Q     A  E  Q     N
       E                          A
                                  A

301    E  R  S  A  Q  K  S  N  N  A  R  Q  Q  L  E  R  N  K         320
                      N  S                    E              T
                      N  S                                   T
                      E

321    D  L  K  K  L  Q  E  G  A  V  K  S  K  F  A  T              340
       E                                            S  K
       E                                            S  R
                                                    A  R
                                                    F
                                                    L
                                                    A
                                                    G
                                                    G
                                                    R

341    I  S  A  L  E  A  K  I  Q  L  E  E  Q  L  E  Q  E  A         360
          A              G              V                 K
          R              A              V                 R
          R                                                F
          K                                                L
                                                           A
                                                           G
                                                           G
                                                           R

361    E  A  A  N  K  L  R  R  T  E  K  K  L  K  E  I  M            380
          A  Q           A  K  Q  R  D        M
          K              V  K  R  Q                R
                         L  A     E
                         H
                         N
                         M

381    M  Q  E  D  E  R  A  D  D  Y  K  E  Q  M  E  K               400
       L     V           R  K  E              A
       L                 R  K  E              A
                                              E

401    N  A  R  M  K  Q  L  K  R  Q  L  E  E  A  E  E              420
          R  V           K                    S     T
             V                                S     O
                                              A     N
                                              T

421    A  N  V  R  R  K  L  Q  R  E  L  D  A  T  E  N  E           440
       I     S                       E
       A     N                       E
             R                       R

441    G  L  S  R  E  V  S  T  L  K  N  R  L  R  G  N  I  S         460
       A  M  G        N  A     S  K  K     G  P  E
       A  M  G        N  A     L  H        P  L  T
       F  S  P                              P     E
          V                                       D
          S  Q
          D  E

461    F  S  R  S  G  R  P  Q  R  H  I  E  G  N  P  L  E           480
       T  D  T     S     Q  G     V              S  D  G
       S  E  E           R        I                 D
                         S

481    S  E  E  T  E  S  K  T  S  D  V  N  E  T  Q  P  P  Q  S     500
                V  D     R  A        F        K  S  S  E  ∗

501    E  ∗
```

ANTIBODY TO SMOOTH MUSCLE MYOSIN HEAVY CHAINS

This application is a continuation of abandoned application, Ser. No. 08/163,407 filed Dec. 8, 1993, which is a continuation of abandoned application, Ser. No. 07/768,075, filed as PCT/JP90/00398 published as WO90/11520.

BACKGROUND OF THE INVENTION

1. Field of the Invention

The present invention relates to an antibody capable of distinctly recognizing a single isoform of smooth muscle myosin heavy chains or an active fragment of the antibody, a labeled antibody or an active fragment thereof and a method for preparing the same.

2. Description of Related Art

Myosin which is a contractile protein constructing the thick filaments of muscle cells has a function of converting chemical energy to mechanical work by reacting with actin filaments to degrade ATP (ATPase activity). The myosin molecule has subunits composed of heavy chains and light chains. It is known that myosin heavy chains are not homogeneous molecules but are present in the form of several kinds of isoforms in skeletal muscle or cardiac muscle heavy chains. These isoforms have different ATPase activities and change their expression types by the progress of development, administration of hormone or stress such as pressure load, etc.

On the other hand, it is known that smooth muscle has physiological characteristics quite dissimilar to those of skeletal muscle or cardiac muscle not only in myofibrils but also in calcium controlling mechanism or continuous contraction mode. However, at the present time, very few studies have been made on molecular structure of smooth muscle myosin or a variety of molecules thereof.

It is reported that smooth muscle myosin heavy chains are separated into two molecules by gel electrophoresis and only one of them is phosphorylated (cf., Eur. J. Biochem., 152, 207–211 (1985), Circulation Res., 59, 115–123 (1986), Am. J. Physiol., 19, C861–C870 (1986), J. Biol. Chem., 262, 7282–7288 (1987), Biochemistry, 27, 3807–3811 (1988) and so on). Nagai et al. report on cloning of cDNA of myosin heavy chains from cDNA library prepared from rabbit smooth muscle and clarifying its nucleotide sequence (cf., Proc. Natl. Acad. Sci., U.S.A., 85, 1047–1051 (1988)).

In general, as a means for elucidating the physiological significance of various isoforms of myosin or the function of controlling expression of myosin isoforms in ontogenesis, etc., an immunological technique using antibodies to myosin isoforms has been adopted.

However, a problem is encountered that the known antibodies to smooth muscle myosin heavy chains cannot distinctly recognize the recently found specific isoform of smooth muscle myosin heavy chains (J. Biol. Chem., 262, 7282–7288 (1987)).

SUMMARY OF THE INVENTION

As a result of various investigations to obtain an antibody having a specificity quite different from the antibodies reported heretofore, namely, an antibody capable of distinctly recognizing a single isoform of smooth muscle myosin heavy chains, the present inventors have succeeded in revealing differences in the amino acid sequences of isoforms of smooth muscle myosin heavy chains and also have succeeded in obtaining antibodies specific to the different amino acid sequences. The obtained antibody can specifically recognize a single isoform of smooth muscle myosin heavy chains distinctly from the other isoforms.

Therefore, the present invention relates to:

an antibody capable of distinctly recognizing a single isoform of smooth muscle myosin heavy chains or an active fragment of the antibody;

the antibody or an active fragment thereof labeled with a label;

a method for preparing the antibody or active fragment of the antibody which comprises immunizing an animal with an oligopeptide containing an amino acid sequence of the isoform or its complex and collecting its antiserum; and, a method for preparing the antibody or active fragment of the antibody which comprises:

immunizing an animal with an oligopeptide containing an amino acid sequence of the isoform or its complex to collect its antibody-producing cell;

fusing the antibody-producing cell with myeloma cell to obtain a hybridoma capable of producing a monoclonal antibody which recognizes isoforms of smooth muscle myosin heavy chains; and, then culturing the hybridoma and collecting the monoclonal antibody.

BRIEF DESCRIPTION OF THE DRAWINGS

FIG. 1 shows the results of SDS-PAGE and immunoblotting of smooth muscle myosin heavy chains from rabbit aorta. Line 1 shows the results obtained by performing SDS-PAGE and then immunoblotting using anti-C1 antiserum; Line 2 shows the results obtained by performing SDS-PAGE and then immunoblotting using anti-C2 antiserum; and Line 3 shows the results obtained by performing SDS-PAGE and then staining with amide black.

FIG. 2 shows the results of SDS-PAGE and immunoblotting of smooth muscle myosin heavy chains from rabbit uterus. Lines 1 to 3 show the results obtained by treatments in a manner similar to FIG. 1.

FIG. 5 shows fluorescence microscopic photographs of the aorta of rabbit in the fetal period, in the neonatal period (on Day 10 after birth) and in the growth period (on Day 30 after birth), which was stained with anti-C1 antiserum or anti-C2 antiserum. Photographs E, G and I are those stained with anti-C1 antiserum and Photographs F, H and J are those stained with anti-C2 antiserum. Photographs E and F indicate the fetal period, Photographs G and H indicate the neonatal period, and Photographs I and J indicate the growth period.

FIG. 8 shows fluorescence microscopic photographs of the aorta of rabbit which was stained with anti-C3 antiserum. Photographs A and B are those in the fetal period and in the growth period.

FIG. 10 shows amino acid sequences of the isoforms of smooth muscle myosin heavy chains except for the N-terminus. The amino acid sequence of isoform SM-3, the amino acid sequence of isoform SM-1 and the amino acid sequence of isoform SM-2 are shown in the upper column, the middle column and the lower column, respectively. With respect to the amino acid sequences of SM-1 and SM-2, only the amino acids different from those in the amino acid sequence of SM-3 are shown. In FIG. 10, symbol (—) designates that there is no corresponding amino acid and symbol * designates the C-terminus of each isoform. Respective amino acids are given by one letter symbol [Lubert Stryer, Biochemistry, 2nd ed., p. 16 (1981), W. H. Freeman and Company, San Francisco] and L-amino acids represented by the respective symbols are follows.

Figure 3A:
FIG. 3 shows fluorescence microscopic photographs of the arterial duct (Botallo's duct) of rabbit on Day 1 after birth, which was stained with anti-C1 antiserum or anti-C2 antiserum. Photographs A and B are those stained with anti-C1 antiserum and anti-C2 antiserum, respectively.

| A: alanine | R: arginine | N: asparagine |
|---|---|---|
| D: aspartic acid | C: cysteine | Q: glutamine |
| E: glutamic acid | G: glycine | H: histidine |
| I: isoleucine | L: leucine | K: lysine |
| M: methionine | F: phenylalanine | T: threonine |
| P: proline | S: serine | V: valine |
| W: tryptophan | Y: tyrosine | |

DETAILED DESCRIPTION OF THE INVENTION

Hereafter the present invention is described in detail.

(1) Characteristic feature of the antibody of this invention

The antibody of the present invention is characterized by distinctly recognizing a single isoform of smooth muscle myosin heavy chains and showing no substantial cross reactivity with myosin heavy chains of cardiac or skeletal muscle. So long as the antibody has the characteristics, it may be any of polyclonal antibody (antiserum) and monoclonal antibody. Herein, the term "distinctly recognizing" is used to mean that there is no substantial cross reactivity between the respective isoforms of smooth muscle myosin heavy chains.

The term "single isoform" refers to a kind of isoforms, if those isoforms which are derived from two or more species of animal are isoforms of the same type, the antibody of the present invention can similarly recognize the isoforms, as will be later described.

The isoform of smooth muscle myosin heavy chains recognized by the antibody of the present invention may be any of isoforms derived from mammals such as human, horse, bovine, goat, sheep, swine, monkey, rabbit, guinea pig, rat, mouse, hamster, dog, cat, etc.; those derived from Aves such as chicken, pigeon, duck, etc. but is not particularly limited. The antibody of the present invention may be also an antibody capable of doubly recognizing the corresponding isoforms of smooth muscle myosin heavy chains derived from the two or more kinds of animals. For example, the antibody prepared in the example later described was the one capable of doubly recognizing the corresponding isoforms of rabbit and human smooth muscle myosin heavy chains. Among them, the isoform capable of recognizing the isoform of human smooth muscle myosin heavy chains permits one to histologically investigate the expression state of the isoform of human smooth muscle myosin heavy chains in various diseases and is thus extremely significant for objective diagnosis and study of causes for diseases or progress after onset.

So far the present inventors have verified the presence of 3 isoforms in smooth muscle myosin heavy chains; determined their amino acid sequences; and made a report on SM-1 and SM-2 [J. Biol. Chem., 264, No. 17, 9734–9737 (issued Jun. 15, 1989)]. The amino acid sequences of the three isoforms except for the N-terminus are shown in FIG. 10. The three isoforms are defined as follows.

(1) Isoform 1 of smooth muscle myosin heavy chain (hereafter referred to as "SM-1"): an isoform which is expressed over the entire periods of the fetal, neonatal and growth periods during the course of ontogenesis and is phosphorylated:

(2) Isoform 2 of smooth muscle myosin heavy chain (hereafter referred to as "SM-2"): an isoform which is not expressed in the fetal period but is expressed in the neonatal and growth periods during the course of ontogenesis:

(3) Isoform 3 of smooth muscle myosin heavy chain (hereafter referred to as "SM-3"): an isoform (fetal type isoform) which is expressed in the fetal and neonatal periods but not expressed in the growth period, during the course of ontogenesis:

The recognition site of the antibody of the present invention is the portion of the amino acid sequence of the isoform which is different from the other isoforms of smooth muscle myosin heavy chains. That is, an example of the "antibody capable of (distinctly) recognizing a single isoform" is the antibody capable of recognizing the site specifically present in each isoform having the amino acid sequence shown in FIG. 10. The amino acid sequence moiety specifically present in each isoform which can be used to prepare the antibody of the present invention is, e.g., regarding SM-1, an optional sequence portion present in 50–60 amino acid residues from the C-terminus; regarding SM-2, an optional sequence portion present in 10–20 amino acid residues from the C-terminus; regarding SM-3, an optional sequence selected from the portions different from the amino acid sequences of SM-1 and SM-2, in FIG. 10.

For example, in rabbit smooth muscle myosin heavy chains, the amino acid sequences of SM-1 and SM-2 are identical except for those around the C-terminus. However, the amino acid sequences around the respective C-termini of SM-1 and SM-2 are represented by formulas [I] and [II]:

(SM-1)

H₂N— ... ... - SKLRRGNETSFVPT         [I]
RRSGGRRVIENADGSEEEVD
ARDADFNGTKSSE - COOH (SM-2)

H₂N— ... ... - SKLRGPPPQETSQ - COOH         [II]

and the amino acid sequences and their lengths subsequent to "SKL" are greatly different from each other.

SM-3 is different from SM-1 and SM-2 in most of the amino acid sequence. In particular, the amino acid sequence around the C-terminus of SM-3 in rabbit smooth muscle myosin heavy chains is represented by formula [III]:

(SM-3)

H₂N— ... ... - NRLRRGGPISFSSSRSG [III]
RPQLHIEGASLELSDDDTESKTSD
VNETQPPQSE - COOH which is different from the amino acid sequences around the C-termini, of SM-1 and SM-2. The antibody of the present invention recognizes, for example, the difference between the respective isoforms in the amino acid sequences around the C-terminus of smooth muscle myosin heavy chains as described above. By recognizing such a difference, the single isoform of the smooth muscle myosin heavy chains can be distinctly recognized for the first time.

(2) Immunogen

An antigen (immunogen) used to prepare the antibody of the present invention is an oligopeptide having the same amino acid sequence or extremely highly homologous amino acid sequence in the portion different between the respective isoforms of smooth muscle myosin heavy chains.

Specific examples of such oligopeptides are an oligopeptide represented by formula [IV] below which is suited for preparing the antibody capable of specifically recognizing SM-1, an oligopeptide represented by formula [V] below which is suited for preparing the antibody capable of specifically recognizing SM-2, and an oligopeptide represented by formula [VI] below which is suited for preparing the antibody capable of specifically recognizing SM-3.

H₂N-RRGNETSFVPTRRSGGR [IV]

RVIENADGSEEEVDARDADFN

GTKSSE - COOH

H₂N-RGPPPQETSQ - COOH [V]

H₂N-NRLRRGGPISFSSSRSGRPQ [VI]

LHIEGASLELSDDDTESKTSDVNE

TQPPQSE - COOH

In the oligopeptides represented by formulas [IV], [V] and [VI] described above, the oligopeptides themselves as a whole may be used as the immunogen; alternatively, continuous 3 or more, preferably 6 or more peptide fragments in the sequences described above may be used as the immunogen.

The oligopeptides may be prepared by any technique selected from a method for chemical synthesis, a method for synthesis by genetic engineering and a method for enzymatically preparing from smooth muscle myosin heavy chains. Where the number of amino acid residues of the oligopeptide to be prepared is short (e.g., about 20 residues), chemical synthesis is particularly advantageous and simple. Where oligopeptides are chemically synthesized and the amino acid sequence of the isoform in smooth muscle myosin heavy chains is known, an optional sequence composed of continuous 3 or more, preferably 6 or more amino acids in the different portion in each isoform in the amino acid sequences may be chosen and chemically synthesized. Even where the amino acid sequences of the respective isoforms are unknown, a part of the amino acid sequence of each isoform is determined by known techniques such as hydrazinolysis, tritium labeling method, carboxypeptidase method, dinitrofluorobenzene method (DNP method), phenylisothiocyanate method (PTC method), dansyl chloride method (DNS method), cyanate method, direct Edman method, dansyl-Edman method (these techniques are described in [Chemistry of Protein II: Lecture on Biochemical Experiment 1, edited by the Japanese Chemical Association, pages 118–211 (1976)], FD and FAB-mass spectrum method [Chemistry of Protein (I): Lecture on Biochemical Experiment 2, second series, edited by the Japanese Biochemical Association; page 375 (1987)], etc. Then, the isoforms may be chemically synthesized in a manner similar to the case where the amino acid sequence is known.

A method for chemical synthesis of the oligopeptide is not particularly limited but may be appropriately chosen from conventional techniques such as azide method, acid chloride method, acid anhydride method, mixed acid anhydride method, DCC (N,N'-dicyclohexylcarbodiimide) method, activated ester method (p-nitrophenyl ester method, N-hydroxysuccinimide ester method, cyanomethyl ester method, etc.), method using Woodward reagent K, carbonyl diimidazole method, redox method, DCC/additive (e.g., HONB, HOBT, HOSu) method, etc. These methods for chemical synthesis may be performed by any of the liquid phase method and the solid phase method. In terms of procedures of the synthesis, there may be adopted any of the stepwise method in which amino acids are condensed with one by one, and the block condensation method in which a block of several amino acids is condensed in sequence. With respect to detailed procedures and techniques of these methods for synthesis, reference may be made to [The Peptides, vol. 1, Academic Press, New York, USA (1966), Peptide Synthesis, Maruzen Co., Ltd., 1975)].

The thus prepared oligopeptide may be used as the immunogen as it is, but where its antigenicity is weak, it is preferred that the oligopeptide be bound or adsorbed to a suitable carrier and the resulting complex be used as the immunogen.

As carriers used for binding the oligopeptide thereto, natural or synthetic high molecular carriers which are conventionally used to prepare antibodies to hapten antigens may be used. Examples of the natural high molecular carriers include animal serum albumins such as bovine serum albumin, rabbit serum albumin, human serum albumin, etc.; animal serum globulins such as bovine serum globulin, rabbit serum globulin, human serum globulin, sheep serum globulin, etc.; animal thyroglobulins such as bovine thyroglobulin, rabbit thyroglobulin, etc.; animal hemoglobins such as bovine hemoglobin, sheep hemoglobin, human hemoglobin, etc.; hemocyanins such as Keyhole limpet hemocyanin, etc. Examples of the synthetic high molecular carriers include various latices of polymers or copolymers of amino acids such as polylysine, polyglutamic acid, lysine-glutamic acid copolymer, etc.; and of polymers or copolymers prepared from aromatic vinyl compounds, α,β-unsaturated carboxylic acids or esters thereof, α,β-unsaturated nitrile compounds, vinyl halide compounds, conjugated diene compounds, etc., such as styrene, chlorostyrene, α-methylstyrene, divinylbenzene, sodium styrenesulfonate, (meth)acrylic acid, ethyl (meth) acrylate, (meth)acrylonitrile, (meth)acrolein, (meth) acrylamide, butadiene, isoprene, vinyl acetate, vinylpyridine, N-vinyl-2-pyrrolidone, vinyl chloride, vinylidene chloride, etc.

Such carriers may be bound to the oligopeptides by any of physical adsorption, covalent bond, ionic bond, and the like.

As a specific example of the physical adsorption, for example, latex particles and the oligopeptide may be gently stirred at room temperature for 1 to 3 hours (details are described in Endocrinology, 93, 1092 (1973), Japanese Patent Application Laid-Open No. 61-43124, etc.). The covalent bond method may be performed by reacting 1 mol of the high molecular carrier with 1- to 50-fold mols of the oligopeptide at a reaction temperature of 0° to 50° C. for 30 minutes to 30 hours in various buffers such as borate buffer, phosphate buffer, etc. in the presence of an excess of a crosslinking agent which can activate various reactive residues present in the carrier such as amino, carboxyl, sulfhydryl, etc. to link the oligopeptide and the carrier.

As the crosslinking agent used to bind the oligopeptide to the carrier, there may be used any crosslinking agent conventionally used for binding hapten or peptide to a carrier or enzyme. Examples of such crosslinking agent include bisdiazonium compounds such as bisdiazotized benzidine, bisdiazotized 3,3'-dianisidine, etc. which can crosslink with tyrosine, histidine, tryptophan, etc.; dialdehyde compounds such as glyoxal, malondialdehyde, glutaraldehyde, succinaldehyde, adipaldehyde, etc. which can crosslink amino groups with each other; diisocyanate compounds such as toluene-2,4-diisocyanate, xylenediisocyanate, etc. which can crosslink amino groups with each other; halonitrobenzene compounds such as 2,4-dinitro-1,5-difluorobenzene, p,p'-difluoro-m,m'-dinitrophenylsulfone, etc. which can crosslink amino groups with each other; imide ester compounds such as diethylmalonimidate, etc. which can crosslink amino groups with each other; dimaleimide compounds such as N,N'-O-phenylenedimaleimide, N,N'-m-phenylenedimaleimide, etc. which can crosslink thiol groups with each other; maleimide carboxyl-N-hydroxysuccinimide compounds such as N-(m-maleimidobenzoyloxy)succinimide, 4-(maleimidomethyl) benzoic acid-N-hydroxysuccinimide ester, m-maleimidobenzoyl-N-hydroxysuccinimide ester, 4-(maleimidomethyl)-cyclohexane-1-carboxyl-N'-hydroxysuccinimide ester, etc. which can crosslink amino and thiol groups; carbodiimide compounds such as N,N'-dicyclohexylcarbodiimide, N-ethyl-N'-dimethylaminocarbodiimide, 1-ethyl-3-diisopropylaminocarbodiimide, 1-cyclohexyl-3-(2-morpholinyl-4-ethyl)carbodiimidomethyl-p-toluenesulfonate, etc. which can crosslink amino and carboxyl groups; isoxazolium salt compounds such as N-ethyl-5-phenylisoxazolium-3'-sulfonate, etc. which can crosslink amino and carboxyl groups; alkyl chloroformate compounds such as ethyl chloroformate, isobutyl chloroformate, etc. which can crosslink amino and carboxyl groups. The crosslinking agent may be appropriately chosen from the above compounds, depending on the kind of the binding site of the oligopeptide used.

The thus prepared immunogen (complex of the oligopeptide and the carrier) may be isolated and purified in a conventional manner such as dialysis, gel filtration and used for the following preparation of the antibody.

(3) Preparation of antibody

As the immunogen, the oligopeptide itself or the complex of the oligopeptide and the carrier prepared as described above is used. As the oligopeptide-carrier complex, it is preferred to use as the immunogen the complex prepared by linking 2- to 50-fold mols of the oligopeptide per mol of the carrier, especially the complex in which 5- to 20-fold mols of the oligopeptide are linked per mol of the carrier.

Where antiserum is prepared using such immunogen, a method for the preparation may be conventional and comprises administering the immunogen to animal of a different species from that derived from the immunogen to produce the antibody capable of distinctly recognizing a single isoform of smooth muscle myosin heavy chains in vivo and collecting the antibody.

That is, animal to which the immunogen is administered may be any of bovine, horse, sheep, goat, rat, mouse, guinea pig, hamster, dog, cat, swine, rabbit, monkey, pigeon, chicken, duck, etc. In particular, mouse, rat, guinea pig and rabbit are preferred.

Administration of the immunogen to such animal may be performed in a conventional manner. An emulsion of various adjuvant such as Freund's complete adjuvant, Freund's incomplete adjuvant, alum adjuvant, aluminum hydroxide adjuvant, pertussis adjuvant, etc., preferably Freund's complete adjuvant, with the immunogen described above is prepared and the emulsion is administered to the animal described above intravenously, intraperitoneally, subcutaneously or intracutaneously.

A preferred dose is 0.01 to 10 mg/animal calculated as the amount of immunogen (oligopeptide or the complex of the oligopeptide and the carrier) in the case of using rabbit or guinea pig as animal and 0.001 to 1 mg/animal in the case of using mouse or rat.

After initial administration, the animal is boostered about 1 to 5 times to a degree similar to the above, every 1 to 4 weeks. Thus, the antibody capable of distinctly recognizing a single isoform of smooth muscle myosin heavy chains can be obtained.

The thus obtained antibody can be collected as antiserum by collecting blood 1 or 2 weeks after the final booster and then performing centrifugation. Where it is necessary to purify the antibody, the antibody present in the antiserum may be fractionated and purified in every class of the antibody by appropriately combining conventional techniques, for example, selective fractionation utilizing difference in solubility (e.g., salting out, alcohol precipitation, etc.), fractionation utilizing difference in charge (e.g., ion exchange chromatography, electrophoresis, etc.), fractionation utilizing difference in molecular weight (e.g., ulltracentrifugation, gel filtration, etc.), fractionation utilizing specific linkage with ligand [e.g., affinity chromatography (using protein A column, etc.)], or the like. Alternatively, only the antibody capable of distinctly recognizing the single isoform in smooth muscle myosin heavy chains may be fractionated and purified, utilizing the immobilized antigen obtained by immobilizing the immunogen described above.

Next, preparation of the monoclonal antibody is described below. The monoclonal antibody may be prepared by appropriately applying known cell fusion, transformation using EB virus, etc.

Taking cell fusion suitable for mass production as an example, the preparation of the monoclonal antibody is explained below. The antibody capable of distinctly recognizing a single isoform in smooth muscle myosin heavy chains can be obtained in large amounts, for example, by the following procedures.

a) Preparation of antibody-producing cell

Animal, preferably mouse, rat, rabbit, hamster, chicken, etc., is immunized with the immunogen described above as in the case of preparing antiserum. The antibody-producing cells such as spleen cells, lymph node cells, peripheral blood cells, etc. from the animal which has acquired the antibody productivity are collected in a conventional manner.

b) Preparation of myeloma cell

As myeloma cells, cell lines derived from various animals such as mouse, rat, chicken, human, etc. which are available to one skilled in the art may be used. As the cell lines used, those having drug resistance and having properties that cannot survive in selective medium in non-fused state but can survive only in the state fused with the antibody-producing cells are preferred. In general, 8-azaguanine-resistant cell line is used. The cell line is deficient of hypoxanthine phosphoribosyl transferase and hence, cannot grow in hypoxanthine aminopterin thymidine (HAT) medium. Further as a property of the cells, the cell line is preferably a so-called non-secretor cell line that does not secrete immunoglobulin.

Specific examples of myeloma cell line are mouse myeloma cell lines such as P3×63Ag8 (ATCC TIB-9) (Nature, 256, 495–497 (1975)), P3×63Ag8 U.1 ($P_3U_1$) (ATCC CRL-1597) (Current Topics in Microbiology and Immunology, 81, 1–7 (1978)), P3×63Ag8.653 (ATCC CRL-1580) (J. Immunology, 123, 1548–1550 (1979)), P2/NSI/1-Ag4-1 (ATCC TIB-18) (European J. Immunology, 6, 511–519 (1976)), Sp2/0-Ag14 (ATCC CRL-1581) (Nature, 276, 269–270 (1978)), etc.; rat myeloma cell lines such as 210.RCY.Ag1.2.3 (Y3-Ag1.2.3) (ATCC CRL-1631) (Nature, 277, 131–133 (1979)), etc.; human myeloma cell lines such as U-266-AR$_1$ (Proc. Natl. Acad. Sci. U.S.A., 77, 5429 (1980)), GM1500 (Nature, 288, 488 (1980)), KR-4 (Proc. Natl. Acad. Sci. U.S.A., 79, 6651 (1982)), etc.

c) Cell fusion

In cell fusion, myeloma cells compatible with the antibody-producing cells are chosen. Cell fusion may be efficiently carried out by mixing $10^7$ to $10^8$/ml of myeloma cells with the antibody-producing cells in a mixing ratio of 1:4 to 10 in medium for culturing animal cells such as Eagle's minimum essential medium (MEM), Dulbecco's modified Eagle's medium (DMEM), RPMI 1640 medium, etc. and contacting the cells with each other at 37° C. for 1 to 10 minutes. For acceleration of the cell fusion, a fusogen such as polyethylene glycol (PEG) having an average molecular weight of 1000 to 6000, polyvinyl alcohol, Sendai virus, etc. may be used.

Using a commercially available cell fusion apparatus utilizing electric pulse, the antibody-producing cells may be fused with myeloma cells.

d) Selection of hybridoma in selective medium

For selecting the desired hybridoma from the cells obtained after the cell fusion, there may be used a method utilizing selective proliferation of cells in selective medium. After appropriately diluting the cell suspension with, e.g., RPMI 1640 medium containing 10 to 15% fetal calf serum (FCS), etc., the diluted cell suspension is inoculated on a microplate in about $10^5$ to $10^6$ cells/well. Selective medium (e.g., HAT medium, etc.) is added to each well and then appropriately exchanged with fresh selective medium to perform cultivation. Where 8-azaguanine resistant strain is used as the myeloma cell and HAT medium is used as selective medium, non-fused myeloma cells die in about 10 days after cultivation and the antibody-producing cells that are normal cells cannot grow in vitro over a long period of time. Therefore, the cells which grow on or after 10 to 14 days after cultivation can be obtained as hybridomas.

e) Screening of hybridoma which can produce the monoclonal antibody capable of distinctly recognizing a single isoform of smooth muscle myosin heavy chain Screening of a hybridoma that can produce the monoclonal antibody capable of distinctly recognizing a single isoform of smooth muscle myosin heavy chain can be performed by enzyme-linked immunosorbent assay (ELISA), radioimmunoassay (RIA), etc. For example, the culture supernatant containing the monoclonal antibody is charged in a 96-well microplate for ELISA, to which the immunogen described above has been adsorbed, to react with the immunogen. Next, enzyme-labeled anti-immunoglobulin antibody is reacted with the bound specific antibody or biotin-labeled anti-immunoglobulin antibody is reacted with the bound specific antibody and then avidin D-enzyme label is reacted therewith. Enzyme substrate is added to each well to form a color. By the color formation, the well added with the culture supernatant containing the hybridoma capable of producing the antibody having a binding ability to the isoform of smooth muscle myosin heavy chain can be determined and the desired hybridoma can be selected.

f) Cloning

Cloning of the hybridoma may be performed by limiting dilution, soft agar method, fibrin gel method, fluorescence activated cell sorter method, etc.

g) Production of monoclonal antibody

To produce the monoclonal antibody from the thus collected hybridoma, conventional cell culture method or ascites formation method, etc. may be adopted.

In the cell culture, the hybridoma is cultured in animal cell culture medium such as 10 to 15% FCS-containing RPMI 1640 medium, serum-free medium, etc. and the antibody can be collected from the culture supernatant.

According to the ascites formation method, mineral oil such as pristan (2,6,10,14-tetramethylpentadecane), etc. is intraperitoneally administered to animal having major histocompatibility coincident with the hybridoma and then, in the case of, e.g., mouse, the hybridoma is intraperitoneally administered in approximately $10^6$ to $10^7$ cells/mouse. The hybridoma forms ascites tumor in about 10 to about 18 days and the antibody is produced there in a high concentration. The antibody can thus be collected from the ascitic fluid.

Where it is necessary to purify the antibody, known techniques such as ammonium sulfate salting out, ion exchange chromatography utilizing anionic exchanger, e.g., DEAE cellulose, etc.; affinity chromatography using protein A-Sepharose, etc., molecular sieve chromatography (gel filtration), etc. may be appropriately chosen and used in combination to purify the antibody.

(4) Antibody fragment

Any fragment the antibody (e.g., various fragments such as $F(ab')_2$, Fab', Fab, etc.) may be used as the active fragment of the antibody so long as it maintains the characteristics of the antibody of the present invention. These active fragments may be prepared by applying to the purified antibody known techniques such as a method for limiting digestion with protease such as papain, pepsin, trypsin, etc. (cf., e.g., Study of Immunobiochemistry: Lecture on Biochemical Experiment 5, second series, edited by the Japanese Biochemical Association, page 89 (1986)).

(5) Labeled antibody or active fragment

As a label for labeling the antibody or active fragment, there may be used enzymes (e.g., $\alpha,\beta$-galactosidase, peroxidase, alkaline phosphatase, glucose-6-phosphate dehydrogenase, etc.); coenzymes or prosthetic groups (e.g., FAD, FMN, ATP, heme, etc.); in vivo ligand receptors (e.g., biotin, avidin, streptoavidin, etc.); fluorescein derivatives (e.g., fluorescein isothiocyanate (FITC), fluorescein thioflubamyl, etc.), Rhodamine derivatives (e.g., tetramethyl Rhodamine B isothiocyanate, etc.), umbelliferone, 1-anilino-8-naphthalenesulfonic acid, etc.; chemiluminescence substances such as luminol derivatives [e.g., luminol, isoluminol, N-(6-amino-hexyl)-N-ethylisoluminol, etc.]; radioisotopes ($^{125}I$, $^{131}I$, $^3H$, $^{111}In$, $^{99m}Tc$), and the like. These labels may be directly bound to the antibody or active fragment or may be indirectly bound thereto via other substances (anti-immunoglobulin antibody, biotin-avidin system, etc.). For binding of the antibody or active fragment of the antibody with the label, appropriate techniques may be chosen from known methods described in, e.g., Study of Immunobiochemistry: Lecture on Biochemical Experiment 5, second series, Tokyo Kagaku Dojin Co., Ltd., published in 1986, pages 102–112; Radioimmunoassay, second series (supra), EP B1,0163014, etc.

(6) Utility of the antibody of the present invention

The antibody of the present invention is capable of distinctly recognizing a single isoform in smooth muscle myosin heavy chains. Therefore, the antibody of the present invention is useful as biochemical reagents or reagents for diagnosis for clarifying the mechanism of controlling the expression of smooth muscle myosin heavy chain isoforms in ontogenesis, more specifically, as reagents for tissue staining, etc.

Among them, in particular, the antibody capable of distinctly recognizing an isoform in human smooth muscle myosin heavy chains is extremely useful for objective diagnosis or study of causes for onset of disease or progress after onset, since the state of expressing the isoforms of human smooth muscle myosin heavy chains in various diseases can be histologically investigated.

Furthermore, these antibodies or their active fragments labeled with labels such as radioisotopes, etc. are useful as in vivo diagnostics for examining the site or degree of vascular disturbance, by administering the same to animal including human and performing image diagnosis.

In addition, the antibodies of the present invention or their active fragments or those labeled with labels are also useful as reagents for immunoassay which can determine qualitatively or quantitatively the smooth muscle myosin heavy chains in body fluids (blood, urine, etc.). Immunoassay may be performed by known methods [cf., Radioimmunoassay, second series, edited by Hiroshi IRIE, Kodansha Publishing Co., Ltd., published May 1, 1979), Enzymeimmunoassay, second edition, edited by Eiji ISHIKAWA et al., Igaku Shoin Publishing Co., published Dec. 15, 1982; Methods in ENZYMOLOGY, Vol. 92, Immunochemical Techniques, Part E: Monoclonal Antibodies and General Immunoassay Methods, published by Academic Press Co.], e.g., by sandwich method. Such immunoassay makes it possible to perform diagnosis of various diseases, for example, vascular impairments, arteriosclerosis, cancer, etc.

EXAMPLES

Hereafter the present invention is described more specifically with reference to the examples.

Example 1

Rat Antisera to the Isoform of Smooth Muscle Myosin Heavy Chains

Using as antigens synthetic peptide C1 ($H_2N$-ARDADFNGTKSSE-COOH) corresponding to 13 amino acid residues from the C-terminus of isoform 1 (SM-1) of rabbit smooth muscle myosin heavy chains, synthetic peptide C2 ($H_2N$-RGPPPQETSQ-COOH) corresponding to 10 amino acid residues from the C-terminus of isoform 2 (SM-2) of rabbit smooth muscle myosin heavy chains, and synthetic peptide C3 ($H_2N$-TSDVNETQPPQSE-COOH) corresponding to 13 amino acid residues from the C-terminus of isoform 3 (fetal type: SM-3) of rabbit smooth muscle myosin heavy chains, these antigens were reacted with bovine serum albumin (BSA) in a manner similar to conventional maleimide method [Methods for Immune Experiments XI, Japanese Immunological Association, published 1982, pages 3529–3534] to prepare the complexes of the synthetic peptides with BSA (C1-BSA, C2-BSA and C3-BSA). In the thus prepared complexes, 10 molecules in average of the synthetic peptide are bound per molecule of BSA.

Next, C1-BSA was dissolved in physiological saline in a concentration of 1 mg/ml and the solution is mixed with Freund's complete adjuvant in a proportion of 1:1 to prepare an emulsion and 200 μl of the emulsion was intracutaneously administered to the back of Wistar rat (female, age of 6 weeks).

Furthermore the same amount of the emulsion was administered 4 times every 2 other weeks for booster.

Blood was collected 10 days after the final booster. After allowing to stand at 4° C. for 16 hours, the blood was centrifuged at 3000 rpm for 10 minutes to give the supernatant. The supernatant is designated as rat anti-C1 antiserum.

C2-BSA was treated as in C1-BSA to give rat anti-C2 antiserum.

C3-BSA was dissolved in physiological saline in a concentration of 1 mg/ml. The solution was mixed with Freund's complete adjuvant in a proportion of 1:1 to prepare an emulsion and 50 μl of the emulsion was intracutaneously administered to the back of BALB/c mouse (female, age of 6 weeks). Then, C3-BSA was treated as in C1-BSA and C2-BSA to give mouse anti-C3 antiserum.

Example 2

Specificity of Rat Anti-C1 and Anti-C2 Antisera

Specificity of rat anti-C1 and anti-C2 antisera was confirmed by immunoblotting.

(1) Preparation of smooth muscle myosin heavy chains

Tissues of rabbit aorta and rabbit uterus were homogenized together with a 10-fold volume of extraction solution (50 mM sodium dihydrogenphosphate, 1 mM ethyleneglycolbis(2-aminoethyl ether)tetraacetic acid (EGTA), 0.125 mM phenylmethanesulfonyl fluoride (PMSF), pH 7.0). The homogenate was centrifuged at 4° C. for 10 minutes at 1000 rpm to give the precipitate. The whole amount of the precipitate was suspended in Guba-Straub solution (150 mM sodium dihydrogenphosphate, 300 mM sodium chloride, 10 mM ATP, 1 mM EGTA, 0.125 mM PMSF, 1 mM 2-mercaptoethanol, pH 6.7). After gently stirring at 4° C. for an hour, the emulsion was centrifuged at 4° C. for 10 minutes at 10000 rpm to give the supernatant containing smooth muscle myosin heavy chains. After adding the equal volume of glycerin, the obtained supernatant was stored at −20° C. until use.

(2) Electrophoresis

The smooth muscle myosin heavy chains contained in the extract obtained in (1) above were separated into the respective isoforms by SDS-polyacrylamide gel electrophoresis (SDS-PAGE).

SDS-PAGE was performed by using polyacrylamide gel obtained by overlaying 3% concentration gel and 4% separation gel and electrophoresing the polyacrylamide gel at 60V for 12 hours.

A sample for the electrophoresis was obtained by adding the same volume of reduction treatment solution (100 mM Tris-hydrochloride buffer (pH 6.8) containing 2% SDS, 5% 2-mercaptoethanol, 20% glycerol, 0.01% bromophenol blue (BPB)) to the extract obtained in (1) and reacting them at 100° C. for 2 minutes.

(3) Immunoblotting

A nitrocellulose membrane was put on the separation gel obtained by SDS-PAGE in (2) and 60 V was applied for 12 hours to transfer the protein onto the nitrocellulose membrane. The thus obtained nitrocellulose membrane was cut into a rectangular shape along with the electrophoretic line of the sample. A part of the membrane was treated with amide black to stain the protein. The remaining membrane was soaked in 3% gelatin solution and reacted at 37° C. for an hour for blocking. Then, rat anti-C1 antiserum and rat anti-anti-C2 antiserum diluted to 1/50 concentration with phosphate buffered saline (PBS) were reacted with the membrane at 37° C. for an hour. After the reaction, the nitrocellulose membrane was soaked in PBS (containing 0.05% Tween 20) for 5 minutes to rinse the membrane. After repeatedly rinsing 3 times in a similar manner, the membrane was reacted at 37° C. for an hour with peroxidase-labeled anti-rat IgG antibody (made by EY Laboratory Co.) diluted to 1/200 concentration with PBS. After the reaction, the nitrocellulose membrane was rinsed 3 times with PBS (containing 0.05% Tween 20). Thereafter the membrane was reacted with substrate solution [containing 30 mg of Color Developer (made by Bio Rad Co.), 10 ml of methanol, 50 ml of PBS and 30 µl of hydrogen peroxide] to form a color. At the time when the color was appropriately formed, the membrane was rinsed with water to terminate the reaction.

The results of SDS-PAGE and immunoblotting are shown in FIGS. 1 and 2.

FIG. 1 shows the results of SDS-PAGE and immunoblotting of smooth muscle myosin heavy chains from rabbit aorta. Line 1 shows the results obtained by performing SDS-PAGE and then immunoblotting using anti-C1 antiserum; Line 2 shows the results obtained by performing SDS-PAGE and then immunoblotting using anti-C2 antiserum; and Line 3 shows the results obtained by performing SDS-PAGE and then treating with amide black.

FIG. 2 shows the results of SDS-PAGE and immunoblotting of smooth muscle myosin heavy chains from rabbit uterus. Lines 1 to 3 show the results obtained by treatments in a manner similar to FIG. 1.

From FIGS. 1 and 2, it was confirmed that anti-C1 antiserum specifically reacted with SM-1 alone and anti-C2 antiserum specifically reacted with SM-2 alone.

Example 3

Immunofluorescent Staining of Tissue

Rabbit tissues (rabbit aorta in the fetal, neonatal and growth periods, rabbit Botallo's duct, rabbit uterus in the growth period) and human tissues (normal blood vessel from adult human and human umbilical cord artery) were prepared in frozen slices using a cryostat. The slices were rinsed by immersing in PBS for 5 minutes. The rinsing was repeated further 3 times. Next, each tissue slice was reacted at 37° C. for an hour with rat antisera (anti-C1 antiserum, anti-C2 antiserum) or mouse antiserum (anti-C3 antiserum) diluted with PBS to 1/10 to 1/50 concentration. The slice was then rinsed by immersing in PBS for 5 minutes. The rinsing was repeated further 3 times. The rinsed tissue slice was reacted at 37° C. for an hour with fluorescein isothiocyanate (FITC)-labeled anti-rat IgG antibody or FITC-labeled anti-mouse IgG antibody (both manufactured by EY Laboratory Co.) diluted with PBS to 1/10 to 1/50 concentration. The slice was then rinsed with PBS and treated with glycerol. The thus obtained tissue slice was observed by a fluorescence microscope. The following (1) to (7) were confirmed.

Figure 3B:
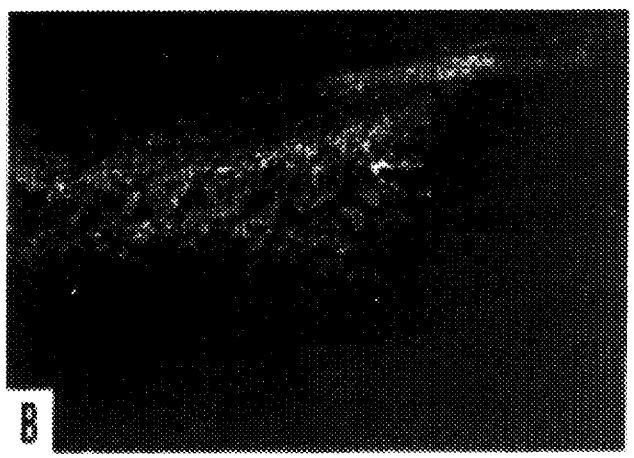

(1) The arterial duct (Botallo's duct) of rabbit on Day 1 after birth was recognized by (stained with) anti-C1 and anti-C2 antisera. It is revealed that SM-2 was little present in ordinary vascular smooth muscle on Day 1 after birth but abundantly present in Botallo's duct characterized by closing immediately after the birth (cf. FIG. 3).

Figure 4A:
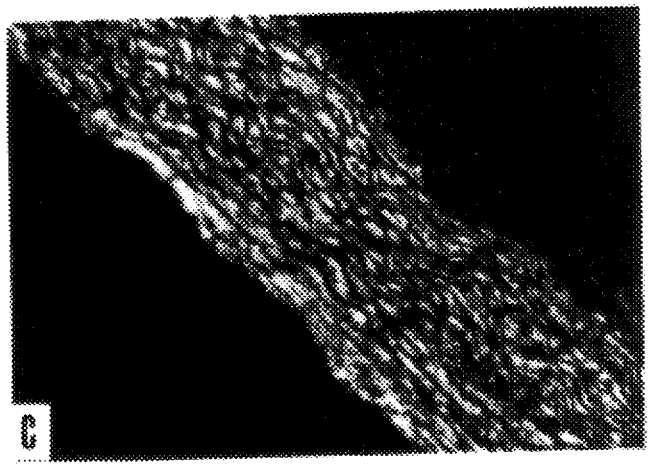
FIG. 4 shows fluorescence microscopic photographs of the aorta of rabbit in the growth period, which was stained with anti-C1 antiserum or anti-C2 antiserum. Photographs C and D are those stained with anti-C1 antiserum and anti-C2 antiserum, respectively.
Figure 4B:
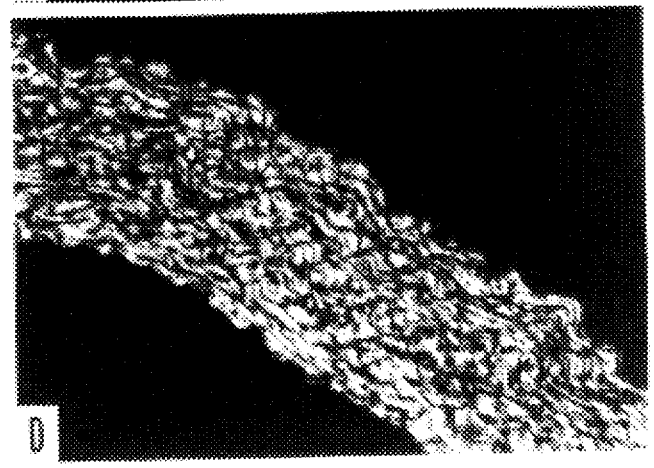

(2) The vascular smooth muscle of rabbit in the growth period was recognized by (stained with) anti-C1 antiserum and anti-C2 antiserum (cf. FIG. 4).

(3) The vascular smooth muscle of rabbit in the fetal period, in the neonatal period (on Day 10 after birth) and in the growth period (on Day 30 after birth) was recognized by (stained with) anti-C1 antiserum. Anti-C2 antiserum recognized the vascular smooth muscle of rabbit in the neonatal period and in the growth period but did not recognize (stain) vascular smooth muscle in the fetal period. That is, by tissue staining using both anti-C1 and anti-C2 antisera, change in expression of the smooth muscle myosin heavy chain isoforms in blood vessel could be revealed (cf. FIG. 5).

Figure 6A:
FIG. 6 shows fluorescence microscopic photographs of the uterus of rabbit in the growth period, which was stained with anti-C1 antiserum or anti-C2 antiserum. Photographs K and L are those stained with anti-C1 antiserum and anti-C2 antiserum, respectively.
Figure 6B:
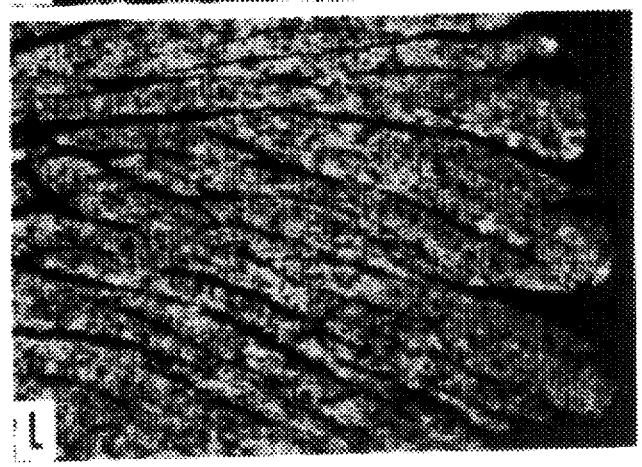

(4) Both of anti-C1 antiserum and anti-C2 antiserum recognized (stained) the uterus smooth muscle of rabbit in the growth period. Taking the results of (2) also into account, it was shown that SM-1 and SM-2 were present in the smooth muscle cells in the growth period (cf. FIG. 6).

Figure 7:
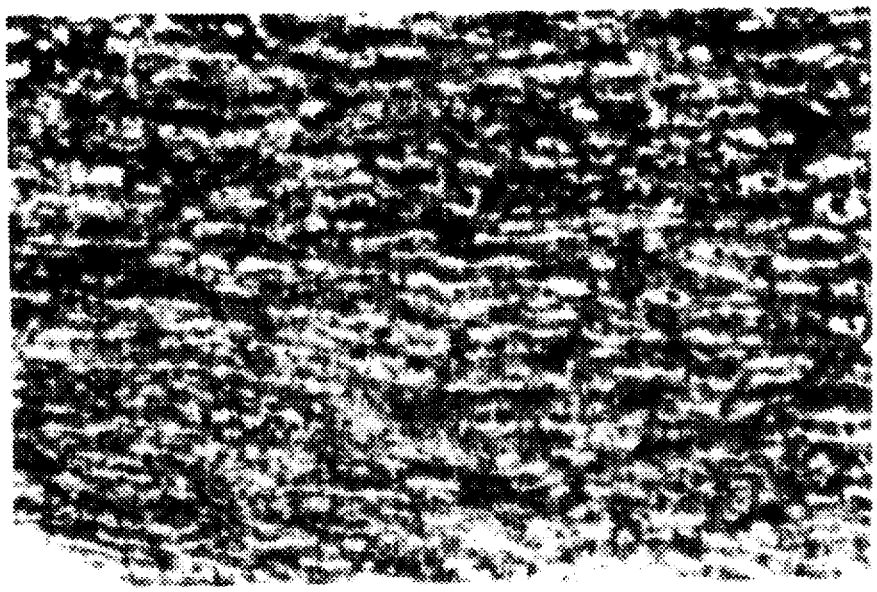
FIG. 7 shows a fluorescence microscopic photograph of normal blood vessel from human adult, which was stained with anti-C2 antiserum.

(5) The normal vascular smooth muscle cells of human adult were recognized by anti-C2 antiserum (cf. FIG. 7).

(6) Anti-C3 antiserum recognized (stained) the vascular smooth muscle of rabbit in the fetal period but did not recognize (stain) the vascular smooth muscle in the growth period (cf. FIG. 8).

Figure 9:
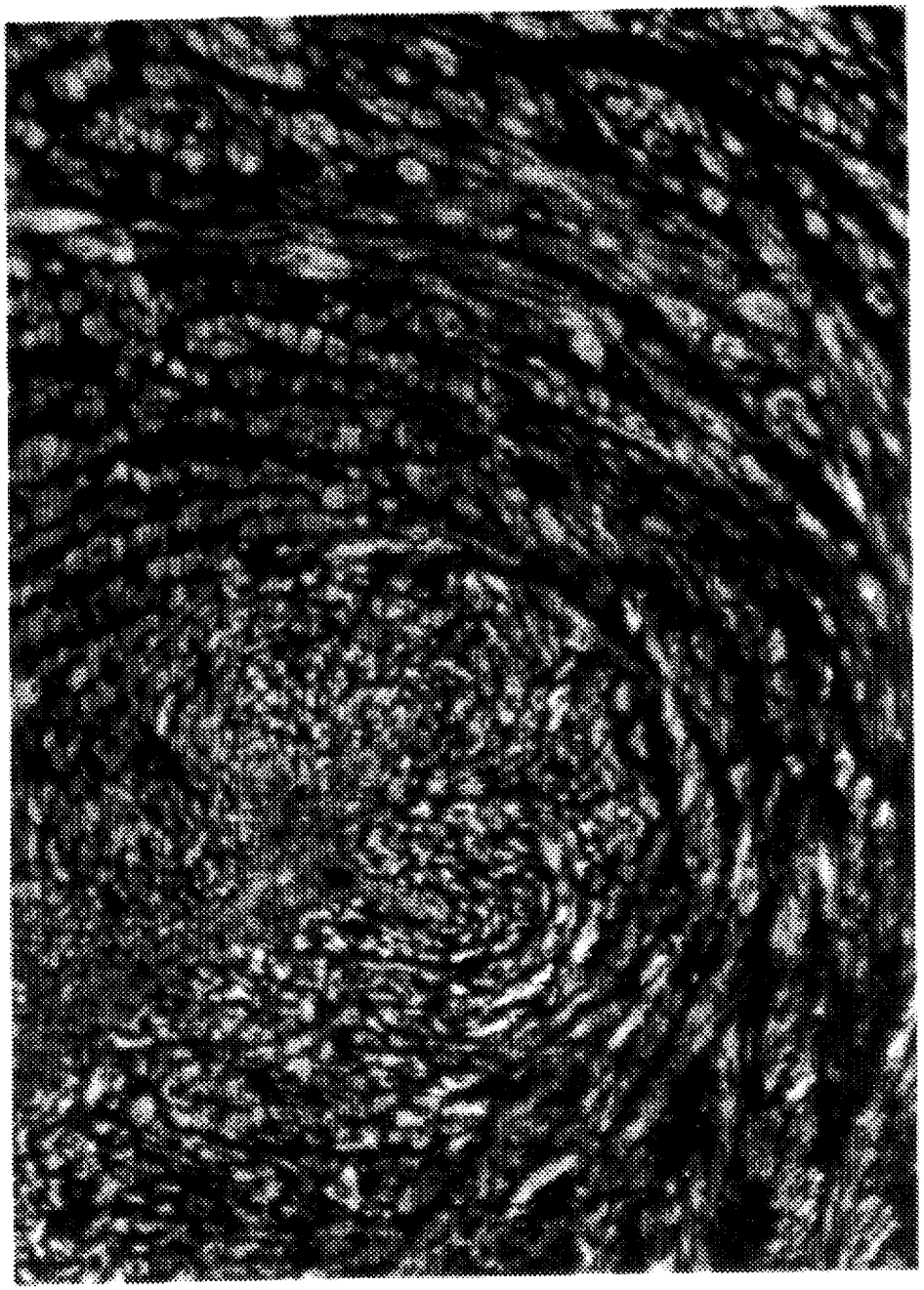
FIG. 9 shows a fluorescence microscopic photograph of umbilical cord artery stained with anti-C3 antiserum.

(7) The human umbilical cord artery was recognized by (stained with) anti-C3 antiserum. It was confirmed that anti-C3 antiserum recognized not only rabbit but also human fetal smooth muscle myosin heavy chain isoform (SM-3) (cf. FIG. 9).

The foregoing results reveal that the antibodies of the present invention are useful as biochemical or diagnostic reagents used for tissue staining and the antisera prepared in Example 1 were capable of distinctly recognizing even the isoforms in human smooth muscle myosin heavy chains.

In a manner similar to the method described above, tissue specimens of rabbit cardiac and skeletal muscles were prepared and staining was performed as described above using anti-C1, anti-C2 and anti-C3 antisera. However, these tissues were not stained at all with anti-C1 antiserum, anti-C2 antiserum or anti-C3 antiserum.

Example 4

Monoclonal Antibody to Smooth Muscle Myosin Heavy Chain Isoform (1) Preparation of monoclonal antibody C1-BSA prepared in Example 1 was dissolved in physiological saline in a concentration of 1 mg/ml. The solution was mixed with Freund's complete adjuvant in a proportion of 1:1 to prepare an emulsion and 50 µl of the emulsion was intraperitoneally administered to BALB/c mouse (female, age of 6 weeks). Further the same amount of the emulsion was administered 3 times similarly every 2 other weeks for booster. Thereafter 100 µl of C1-BSA (100 µg/ml) was intravenously given for final booster.

Three days after the final booster, mouse spleen cells were taken out and rinsed with Eagle's minimum essential medium (MEM). Mouse myeloma P3×63Ag8U.1 ($P_3U_1$) (ATCC CRL-1597) was rinsed with MEM. After the spleen cells were blended with $P_3U_1$ in 10:1, the mixture was centrifuged and 1 ml of MEM solution containing 50% polyethylene glycol (PEG) 1000 was gradually added to the resulting pellets to perform cell fusion. Further MEM solution was added to make the volume 10 ml and then centrifuged. The resulting pellets were suspended in 10% fetal calf serum (FCS)-containing RPMI 1640 medium in 3×1n4 cells/0.1 ml when calculated as $P_3U_1$. The emulsion was charged in each well of a 96-well microplate in an amount of 0.1 ml each. One day after, 0.1 ml of HAT medium was supplemented and the half of the medium was then exchanged with fresh HAT medium every 3 to 4 other days.

On Day 10 after the fusion, 50 μl of the culture supernatant was added to a 96-well polyvinyl chloride (PVC) plate which had been previously coated with synthetic peptide C1 (1 μg/ml) and blocked with 3% gelatin. Thereafter, 50 μl of biotinylated horse anti-mouse IgG (manufactured by Vector Co.) solution was added to react them at room temperature for an hour.

After the reaction, each well was thoroughly washed with PBS and 50 μl of avidin-D-peroxidase (manufactured by Vector Co.) solution was added to react them at room temperature for 30 minutes. The well was washed 3 times with PBS and 200 μl of substrate solution [containing 4-aminoantipyrine (0.25 mg/ml), phenol (0.25 mg/ml) and 0.425M hydrogen peroxide] was added to react them. After reacting them at room temperature, absorbance of each well was measured at 550 nm using a 96-well microplate photometer to obtain a hybridoma capable of producing the monoclonal antibody specifically reactive with synthetic peptide C1 (Table 1).

In a manner similar to above, hybridomas capable of producing the monoclonal antibodies specifically reactive with synthetic peptide C2 and with synthetic peptide C3 were obtained, respectively (Table 1).

TABLE 1

| Synthetic peptide | Number of positive well of specific antibody | / | Number of well where cell grows | / | Number of total well |
|---|---|---|---|---|---|
| C1 | 44 | / | 202 | / | 470 |
| C2 | 8 | / | 183 | / | 470 |
| C3 | 37 | / | 470 | / | 470 |

The thus obtained hybridomas were cloned by the limiting dilution method to establish 10 hybridomas (1B4, 1C8, 1C10, 1H9, 2G10, 3C8, 4C6, 4E10, 5C4, 5D5, 5D10) capable of producing the antibody to synthetic peptide C1, 2 hybridomas (1A10, 2B8) capable of producing the antibody to synthetic peptide C2 and 9 hybridomas (1G5, 2A6, 2C5, 2D7, 2G11, 3A4, 3H2, 4H3, 5F6) capable of producing the antibody to synthetic peptide C3.

Next, hybridoma 1B4 thus established was cultured to increase the count. The hybridoma was intraperitoneally administered to mice in $3 \times 10^6$ cells/mouse, to which pristan had been previously administered intraperitoneally, about one month after the administration.

About 10 ml/mouse of ascitic fluid was collected two weeks after.

After diluting about 40 ml (corresponding to the fluid from four mice) of the ascitic fluid with PBS by adding the same volume of PBS, 80 ml of saturated ammonium sulfate solution was added to the dilution. The precipitates under the condition of 50% ammonium sulfate saturation were collected by centrifugation. To the precipitate fraction was added about 10 ml of 0.1M Tris-hydrochloride bufer (pH 7.2) to dissolve. The solution was dialyzed to the same buffer for 2 days.

Next, the antibody solution was added to a column (22 mm×65 cm) packed with DEAE-cellulose DE52 (manufactured by Whatmann Co.). The fraction passed through the column was collected and subjected to gel filtration by adding the fraction to a column (22 mm×65 cm) packed with Ultrogel AcA44 (manufactured by LKB Co.) to obtain the purified antibody specifically reactive with synthetic peptide C1.

Using hybridoma 1A10, the purified antibody specifically reactive with synthetic peptide C2 was obtained in a manner similar to above.

Using hybridoma 2D7, the purified antibody specifically reactive with synthetic peptide C3 was obtained in a manner similar to above.

(2) Property of the monoclonal antibodies to smooth muscle myosin heavy chain isoforms 1) Class and type After the culture supernatant of each hybridoma described above was added to a 96-well PVC plate which had been coated with synthetic peptide C1, synthetic peptide C2 or synthetic peptide C3 and blocked with 3% gelatin, class and type of the antibodies were surveyed using MonoAb-ID EIA Kit (manufactured by Zymed Co.) (Tables 2, 3 and 4).

TABLE 2

Class and type of monoclonal antibody reactive with synthetic peptide C1

| Hybridoma | 1B4 | 1C8 | 1C10 | 1H9 | 2G10 | 3C8 |
|---|---|---|---|---|---|---|
| Class, type | IgG2b,κ | IgG1,κ | IgG2b,κ | IgG1,κ | IgG1,κ | IgG2b,κ |

| Hybridoma | 4C6 | 4E10 | 5C4 | 5D5 | 5D10 |
|---|---|---|---|---|---|
| Class, type | IgG2b,κ | IgG2b,κ | IgG2a,κ | IgG2b,κ | IgG1,κ |

TABLE 3

Class and type of monoclonal antibody reactive with synthetic peptide C2

| Hybridoma | 1A10 | 2B8 |
|---|---|---|
| Class, type | IgG1,κ | IgG1,κ |

TABLE 4

Class and type of monoclonal antibody reactive with synthetic peptide C3

| Hybridoma | 1G5 | 2A6 | 2C5 | 2D7 | 2G11 |
|---|---|---|---|---|---|
| Class, type | IgG1,λ | IgG1,λ | IgG1,κ | IgG2b,κ | IgG3,κ |

| Hybridoma | 3A4 | 3H2 | 4H3 | 5F6 |
|---|---|---|---|---|
| Class, type | IgG1,κ | IgG2b,κ | IgG1,κ | IgG1,κ |

2) Specificity

Specificity of the monoclonal antibodies produced by the hybridomas was confirmed by immunoblotting and immunofluorescence tissue staining.

Immunoblotting was performed with the monoclonal antibody reactive with synthetic peptide C1 and synthetic peptide C2. The procedures were performed in a manner similar to Example 2 except for using the culture supernatant of hybridoma instead of antisera in Example 2 and using as a second antibody peroxidase-labeled anti-mouse IgG antibody (manufactured by EY Laboratory Co.).

Immunofluorescence tissue staining was performed in a manner similar to Example 3 except for using the culture supernatant of hybridoma instead of antisera in Example 3 and using as a second antibody FITC-labeled anti-mouse IgG antibody. Samples provided for the tissue staining are tissue slices of rabbit aorta in the fetal and growth periods.

As the result, quite the same results as those obtained in the case of using antisera (cf. Examples 2 and 3) were obtained. It was confirmed that the monoclonal antibodies of the present invention were all capable of distinctly recognizing a single isoform of smooth muscle myosin heavy chains.

Example 5

Preparation of $^{131}$I-labeled/monoclonal Antibody Specific to SM-1 of Smooth Muscle Myosin Heavy Chains The hybridoma IC10 was administered in a dose of 5×10$^6$ cells/mouse, to which pristan had been previously administered, to induce ascites tumor. The ascitic fluids obtained from the mouse 10 to 20 days after were pooled and the fraction precipitated under the condition of 50% ammonium sulfate saturation was obtained from the ascitic fluids. The precipitate fraction was purified by DEAE-cellulose DE52 column chromatography to obtain the purified monoclonal antibody (MHM-1C10).

To 3 mCi of $^{131}$I are added 200 µl of the purified antibody (8.7 mg/ml), 150 µl of chloramine T (1 mg/ml), 600 µl of sodium metasulfate (1 mg/ml), 150 µl of potassium iodide (50 mg/ml) and 150 µl of 0.5M phosphate buffer (pH 7.5). After reacting them at room temperature, the reaction mixture is subjected to column chromatography using Sephadex G-50 (manufactured by Pharmacia Co.) which has been previously equilibrated with 0.5% bovine serum albumin-containing phosphate buffer to isolate free $^{131}$I. Thus $^{131}$I-labeled monoclonal antibody (MHM-1C10) is obtained.

Example 6

Preparation of $^{111}$In-labeled Fab Fragment of the Monoclonal Antibody Specific to SM-1 of Smooth Muscle Myosin Heavy Chains The monoclonal antibody (MHM-1C10) was purified in a manner similar to Example 5 and then lyophilized. To 2.5 ml of phosphate buffer (pH 7.0) is added 30 mg of the purified antibody. The mixture is reacted at 37° C. for 2 hours.

The reaction solution is subjected to gel filtration column chromatography using protein A-Sepharose (manufactured by Pharmacia Co.) column which has been previously equilibrated with phosphate buffer (pH 7.4) to adsorb Fc fragment and the antibody not yet digested. The non-adsorbed fraction is collected and concentrated to 5 mg/ml with Amicon B15 (manufactured by Amicon Co.). The concentrate is gradually mixed with mixed carboxycarbonic anhydride of diethylenetriamine-pentaacetic acid (DTPA) according to the method of Krejcarek et al. (Biochem. Biophys. Res. Commun., 77, 581–587 (1977)) followed by reacting at 4° C. overnight.

Next, the reaction solution is dialyzed to 0.1M acetate buffer (pH 5.0) and Fab-DTPA fraction is further collected using Sephadex G-25. The fraction is dialyzed to 0.1M glycine hydrochloride buffer (pH 3.5). The thus obtained MHM-1C10 Fab-DTPA is mixed with indium chloride $^{111}$In. The mixture is reacted for 30 minutes. As the result, MHM-1C10 Fab-DTPA-$^{111}$In is obtained.

Industrial Application:

The antibodies of the present invention can distinctly recognize the single isoform of smooth muscle myosin heavy chains and are thus useful as biochemical reagents or reagents for diagnosis for clarifying the mechanism of controlling the expression of smooth muscle myosin heavy chain isoforms in ontogenesis, more specifically, as reagents for tissue staining, etc. In particular, the antibodies or their active fragments capable of distinctly recognizing the single isoform in human smooth muscle myosin heavy chains permit to histologically survey the isoforms of human smooth muscle myosin heavy chains in various diseases and are useful for determination of causes for diseases and diagnosis of the progress after onset.

Furthermore, these antibodies or active fragments thereof labeled with radioactive isotopes, etc. are useful as in vivo diagnostics and also useful as reagents for immunoassay.

We claim:

1. An antibody or antibody fragment which specifically binds to a single isoform of smooth muscle myosin heavy chain, said single isoform of smooth muscle myosin heavy chain being selected from the group consisting of SM-1, SM-2 and SM-3, said antibody or antibody fragment specifically binding within one of the following amino acid sequences (a), (b) or (c) contained in SM-1, SM-2 or SM-3, respectively:

(a) H$_2$N-RRGNETSFVPTRRSGGR
RVIENADGSEEEVDARDADFN
GTKSSE - COOH (b) H$_2$N-RGPPPQETSQ - COOH (c) H$_2$N-NRLRRGGPISFSSSRSGRPQ
LHIEGASLELSDDDTESKTSDVNE
TQPPQSE - COOH.

2. The antibody or antibody fragment according to claim 1, wherein said smooth muscle myosin heavy chain is derived from a human.

3. The antibody or antibody fragment according to claim 1, wherein said single isoform is SM-1.

4. The antibody or antibody fragment according to claim 1, wherein said single isoform is SM-2.

5. The antibody or antibody fragment according to claim 1, wherein said single isoform is SM-3.

6. The antibody or antibody fragment according to claim 1, which antibody or antibody fragment is labeled with a marker.

7. A method for preparing an antibody or antibody fragment according to claim 1, characterized by using as an immunogen a peptide including one of the following amino acid sequences (a), (b) or (c):

(a) H$_2$N-ARDADFNGTKSSE - COOH (b) H$_2$N-RGPPPQETSQ - COOH (c) H$_2$N-TSDVNETQPPQSE - COOH.

or a complex of said peptide with a carrier.

8. The method according to claim 7, wherein said antibody or antibody fragment is a polyclonal antibody.

9. The method according to claim 7, wherein said antibody or antibody fragment is a monoclonal antibody.

* * * * *